(12) United States Patent
Mo et al.

(10) Patent No.: US 8,305,486 B2
(45) Date of Patent: Nov. 6, 2012

(54) AUTO-FOCUS INTRA-ORAL CAMERA HAVING A LINEAR PIEZOELECTRIC ACTUATOR

(75) Inventors: Yufeng Mo, Shanghai (CN); Tan Wang, Shanghai (CN); Zhaohua Liu, Shanghai (CN)

(73) Assignee: Carestream Health, Inc., Rochester, NY (US)

( * ) Notice: Subject to any disclaimer, the term of this patent is extended or adjusted under 35 U.S.C. 154(b) by 224 days.

(21) Appl. No.: 12/763,232

(22) Filed: Apr. 20, 2010

(65) Prior Publication Data

US 2011/0157457 A1 Jun. 30, 2011

(30) Foreign Application Priority Data

Dec. 30, 2009 (CN) .......................... 2009 1 0206779
Dec. 30, 2009 (CN) ....................... 2009 2 0353234 U

(51) Int. Cl.
*A61B 1/04* (2006.01)
*A61B 1/06* (2006.01)
*G03B 13/00* (2006.01)
*H04N 5/232* (2006.01)
*H04N 5/225* (2006.01)

(52) U.S. Cl. .......... 348/351; 348/76; 348/357; 348/374; 600/167

(58) Field of Classification Search ............ 348/65, 348/66, 68, 76, 345, 349, 351, 353, 357, 348/373–376; 600/109, 110, 112, 160, 167
See application file for complete search history.

(56) References Cited

U.S. PATENT DOCUMENTS

| | | | |
|---|---|---|---|
| 4,846,155 A | 7/1989 | Kimura | |
| 5,101,278 A | 3/1992 | Itsumi et al. | |
| 5,307,170 A * | 4/1994 | Itsumi et al. | ............... 348/219.1 |
| 6,019,721 A | 2/2000 | Holmes et al. | |
| 6,806,988 B2 | 10/2004 | Onuki et al. | |
| 7,236,696 B2 | 6/2007 | Higuma et al. | |
| 2008/0079897 A1 | 4/2008 | Goldfain et al. | |

FOREIGN PATENT DOCUMENTS

| | | |
|---|---|---|
| EP | 1 832 221 | 9/2007 |
| JP | 04165773 | 6/1992 |
| WO | WO 03/067323 A1 | 8/2003 |

OTHER PUBLICATIONS

European Search Report, EP Application No. EP 11 00 0364, Jul. 15, 2011, 2 pages.

* cited by examiner

*Primary Examiner* — Daniel M Pasiewicz

(57) ABSTRACT

An auto-focus camera has an optical system for forming an image of a target, a moveable sensor for recording a set of one or more images of the target, the set of one or more images corresponding to a set of one or more positions for the moveable sensor, and a linear piezoelectric actuator mechanically coupled to the moveable sensor for driving the moveable sensor to the set of one or more positions along a predetermined moving direction in response to a stimulus. A driving system is actuable to generate the stimulus to drive the piezoelectric actuator. An image processor, in response to stored instructions, obtains the set of one or more recorded images from the moveable sensor, processes the set of one or more obtained recoded images, and identifies the image that is in focus.

20 Claims, 2 Drawing Sheets

AUTO-FOCUS INTRA-ORAL CAMERA HAVING A LINEAR PIEZOELECTRIC ACTUATOR

FIELD OF THE INVENTION

The invention relates generally to the field of medical diagnostic instruments, and in particular to an apparatus for dental imaging. More specifically, the invention relates to an auto-focus intra-oral camera having a linear piezoelectric actuator for convenient operation and high precision imaging.

BACKGROUND OF THE INVENTION

While there have been improvements in detection, treatment and prevention techniques, dental caries remains a prevalent condition affecting people of all age groups. If not properly and promptly treated, caries could lead to permanent tooth damage and even to loss of teeth. Thus dental imaging based on an intra-oral camera is of great interest.

There exist known intra-oral cameras, such as those available from ACTEON Inc. of Mount Laurel, N.J., USA. Generally, intra-oral cameras are operated over a large working distance range that typically varies between about 1 mm to about 50 mm. They must also have a sizable depth of field (DOF), which is different at different working distances. Thus, focus adjustment is necessary to guarantee a good image quality. However, for most of the known intra-oral cameras including the one disclosed in U.S. Pat. No. 6,019,721 (Holmes et al.), focus adjustment is performed manually by operator adjustment to the distance between a lens and an imaging sensor. Conventional cameras do not have auto-focusing capability and must be separately adjusted for each image. Therefore they are not convenient in use.

There also exist known auto-focus cameras, such as those disclosed in U.S. Patent Application Publication No. US2008/0079897 (Goldfain et al.), U.S. Pat. No. 6,806,988 (Onuki et al.), and U.S. Pat. No. 7,236,696 (Higuma et al.). These earlier cameras, although relatively thin from front to back, are much too wide for intra-oral imaging applications. Their function of auto-focusing is usually achieved by adjusting the focal point of an optical lens relative to a fixed sensor. This may be done by moving the lens or lens assembly or, with a liquid lens, by changing its shape. Conventional cameras with auto-focus capability, although suitable for their intended uses in general imaging applications, cannot be easily used to image an intra-oral target due to their overall width.

While conventional auto-focusing cameras may have achieved certain degrees of success in their particular applications, they fail to meet the dimensional and operational requirements of intra-oral imaging. There is a need for an auto-focus intra-oral camera that is small in width, convenient in use, and capable of capturing images at high precision and at high speed.

SUMMARY OF THE INVENTION

An object of the present invention is to provide an auto-focus intra-oral camera comprising a moveable sensor that can be moved by a piezoelectric actuator for precision imaging.

Another object of the present invention is to provide an auto-focus intra-oral camera comprising a piezoelectric actuator which enables imaging a target within not more than 0.2 second, more preferably not more than 0.1 second, and most preferably not more than 0.05 second.

A further object of the present invention is to provide an auto-focus intra-oral camera with a width not more than 20 mm, more preferably not more than 15 mm, and most preferably not more than 5 mm.

The advantages of the present invention are that the inventive camera is small in its width, convenient in use, and capable of automatically capturing image(s) in the mouth of a patient at high precision and at high speed.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided an auto-focus camera comprising: an optical system for forming an image of a target; a moveable sensor for recording a set of one or more images of the target, the set of one or more images corresponding to a set of one or more positions for the moveable sensor; a linear piezoelectric actuator mechanically coupled to the moveable sensor for driving the moveable sensor to the set of one or more positions along a predetermined moving direction in response to a stimulus; a driving system actuable to generate the stimulus to drive the piezoelectric actuator; and an image processor that, in response to stored instructions, obtains the set of one or more recorded images from the moveable sensor, processes the set of one or more obtained recoded images, and identifies the image that is in focus.

According to another aspect of the invention, there is provided an auto-focus camera comprising: an optical system for forming an image of a target; a moveable sensor for recording the image of the target; a linear piezoelectric actuator mechanically coupled to the moveable sensor for driving the moveable sensor along a predetermined moving direction in response to a stimulus; a driving system actuable to provide the stimulus to drive the piezoelectric actuator to move the moveable sensor; and an image processor that is connected to the driving system and the moveable sensor, wherein the processor responds to stored instructions to actuate the driving system to generate the stimulus that drives the piezoelectric actuator, which in turn moves the moveable sensor to a preferred position where the sensor records the image of the target.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
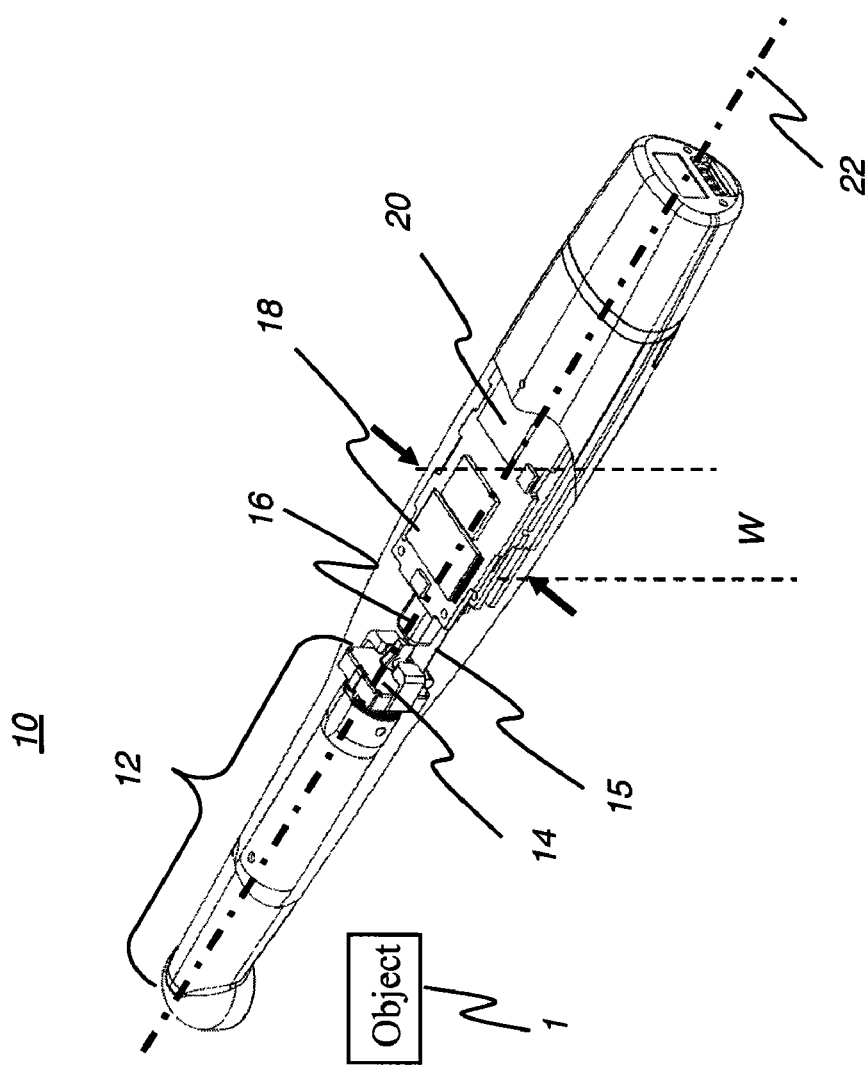
FIG. 1 shows a perspective view of an auto-focus camera of the present invention.

The following is a detailed description of the preferred embodiments of the invention, reference being made to the drawings in which the same reference numerals identify the same elements of structure in each of the several figures.

Figure 2:
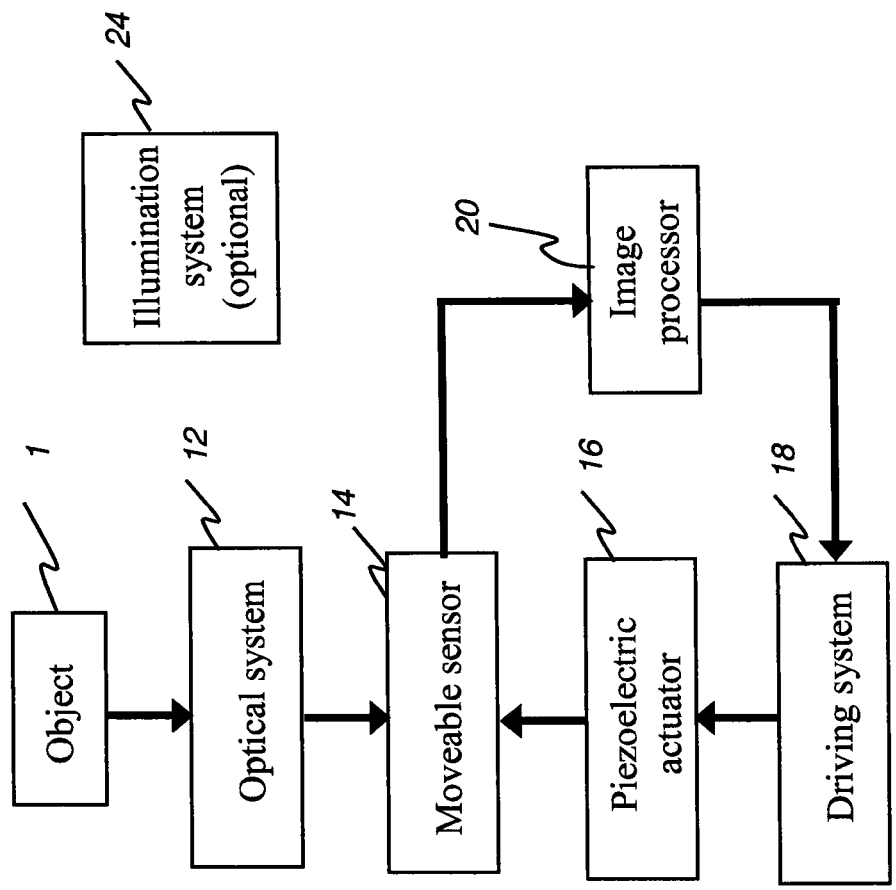
FIG. 2 shows a system configuration of the auto-focus camera according to the present invention.

FIG. 1 shows an auto-focus camera 10 of the present invention according to one embodiment. Auto-focus camera 10 comprises an optical system 12, a moveable sensor 14, a linear piezoelectric actuator 16, a driving system 18, and an image processor 20. FIG. 2 shows a system configuration of auto-focus camera 10 of the present invention and explains the working principle of the present invention according to one embodiment.

Auto-focus camera 10 is intended for imaging a target 1 that is within the mouth of a patient, and to do this expediently and accurately. Target 1 can be a tooth, for example. The imaging operation is completed within not more than 0.2 second, more preferably within not more than 0.1 second, and most preferably within not more than 0.05 second. This high speed imaging for auto-focus is mainly due to the use of piezoelectric actuator 16 that responds at a speed of about 50 to 100 mm/s. At this speed, piezoelectric actuator 16 is capable of rapidly moving sensor 14 within a typical moving range for the intra-oral imaging environment, such as within about +/−3 mm. The high accuracy of images taken from auto-focus camera 10 is achieved due to the precise positioning resolution of piezoelectric actuator 16. In one embodiment, piezoelectric actuator 16 causes linear movement at an average step of about 0.5-1.0 µm.

Optical system 12 comprises a lens or a group of lenses that provide a large depth of field (DOF). Design of such a lens system is familiar to those skilled in the optical design arts. In one example, optical system 10 comprises three lenses. In operation, optical system 10 images target 1 onto moveable sensor 14 multiple times, with images captured at different positions of sensor 14.

Optionally, auto-focus camera 10 also comprises an illuminating system 24, which is configured to direct light from a light source in order to illuminate target 1 for improved imaging at moveable sensor 14. The light source can be one or more light emitting diodes (LEDs) or any other known light source. Illumination system 24 can be integrated into the auto-focus camera 10 package or can be provided from a separate device. A fiber or other light guide could be provided for directing illumination toward target 1 from an external light source.

Moveable sensor 14 records the image of target 1 at each of a number of positions relative to optical system 12. Moveable sensor 14 can be a complementary metal-oxide-semiconductor (CMOS) device, charge coupled device (CCD), or any other known sensor array type. When moveable sensor 14 is located at a preferred position, the image of target 1 is in focus on moveable sensor 14. When moveable sensor 14 is located within a tolerable distance from the preferred position, the image of target 1 may be acceptable, despite its being slightly out of focus on moveable sensor 14. When moveable sensor 14 is located outside of the tolerable distance from the preferred position, the image of target 1 is out of focus on moveable sensor 14 and is not acceptable.

Linear piezoelectric actuator 16 is a piezoelectric motor that is mechanically coupled to moveable sensor 14 in one embodiment and is in communication with driving system 18. Driving system 18 provides the stimulus, such as a signal or current, that actuates linear piezoelectric actuator 16 to move along a predetermined direction 22. Predetermined direction 22 is substantially parallel to the axial direction of auto-focus camera 10, as shown. Driving system 18 can be any known system or component that is actuable or energizable to generate a signal or, more generally, a stimulus that is suitable for driving a piezoelectric motor. In one example, driving system 18 comprises an integrated circuit (IC) driver. IC drivers for piezoelectric actuators are familiar to those skilled in the electronic arts.

Piezoelectric actuator 16, a type of motor that uses piezoelectric response in order to cause linear motion, typically comprises only a few parts: drive elements, drive pads, drive rod, and spring. In one example, when activated in response to a stimulus, such as an electrical signal, the drive elements oscillate at an ultrasonic frequency. The drive pads, which are used for transferring movement from the drive elements to the drive rod, may move in a sinusoidal fashion due to flexural waves in the drive elements. The drive pads are only in contact with the drive rod during half the cycle; the drive rod will therefore move one step forward or backward in each electrical cycle. The spring is used to create friction or a loading force between the drive pads and the drive rod. In response to the electric signal or other stimulus, the drive rod of piezoelectric actuator 16 moves precisely (at an average step of about 0.5-1.0 µm for a typical device) and expediently (at a speed of about 50 to 100 mm/s) along the predetermined moving direction 22.

Though more generally a piezoelectric actuator can be capable of generating movement in three directions, linear piezoelectric actuator 16, according to embodiments of the present invention, only generates movement in predetermined direction 22. As a result of the movement of piezoelectric actuator 16, moveable sensor 14 is translated in position, either pushed or pulled, to move along predetermined direction 22. This activity, in turn, changes the distance between moveable sensor 14 and optical system 12. At some point along predetermined direction 22, moveable sensor 14 is disposed nearest to the focal point of optical system 12.

By using linear piezoelectric actuator 16, auto-focus camera 10 of the present invention can be made small in width W. For intra-oral use, width W should be not more than 20 mm, more preferably not more than 15 mm, and most preferably not more than 5 mm. This narrow width requirement is needed in order to fit the camera comfortably within the mouth of the patient and differentiates auto-focus camera 10 of the present invention from many other types of conventional prior auto-focus cameras that are intended for other uses.

Image processor 20, such as a digital signal processor (DSP), is in communication with both moveable sensor 14 and driving system 18 and interacts with both of these components according to stored, preprogrammed instructions. In one example, the connections among image processor 20, moveable sensor 14, and driving system 18 are made through a hard wire 15, such as a flexible print circuit (FPC) connection. In its image-obtaining function, by being connected to moveable sensor 14, image processor 20 obtains a set of recorded images of target 1 from moveable sensor 14. Each member or element image in the set of recorded images is obtained and stored when moveable sensor 14 is in a different position.

Using commonly known methods such as calculating image sharpness by using a high pass filter, the degree of focusing can be evaluated for each of the images that have been obtained. Image processor 20 calculates sharpness for each element of the set of one or more obtained recorded images. The recorded image in this set that has the highest sharpness is determined to be in focus and is associated with the preferred position for moveable sensor 14. In its movement control function, by being connected to driving system 18, image processor 20 is able to send driving system 18 one or more pulses as movement stimuli. The number of pulses is associated with movement of moveable sensor 14 to different positions. In this way, image processor 20 commands driving system 18 to drive moveable sensor 14 to different positions. Linear piezoelectric actuator 16 accurately and expediently drives moveable sensor 14 backward or forward along predetermined direction 22, as needed, in order to reach each different position. At its preferred position, nearest optimal focus, moveable sensor 14 records a sharp image of target 1. Generally, this is the image that can then be displayed to the camera operator, further processed, and stored for future reference.

In the embodiment of FIG. 1, image processor 20 is a dedicated microprocessor that is integrated into the tight dimensions of the auto-focus camera 10 package. Alternately, image processor 20 can be external to the hand-held camera, such as on part of an operator console or associated with a display, for example. Image processor 20 can be an externally connected computer workstation, laptop computer, or other logic processing device, including a networked processor, for example. Image processor 20 is in communication with moveable sensor 14 and driving system 18 for obtaining and providing the needed data and signals therewith. This communication between moveable sensor 14 and driving system 18 and an external image processor 20 can be through one or more wires or, optionally, can be wireless.

Though auto-focus camera 10 of the present invention is aimed at imaging an intra-oral target, it may be used in other suitable applications, particularly where the camera width requirement is fairly constrained, such as for endoscope applications.

Unlike conventional auto-focus devices, auto-focus camera 10 of the present invention adjusts for focus by shifting the position of moveable sensor 14, rather than by making any adjustment to the camera optics. The use of piezoelectric actuation enables fast and accurate re-positioning of sensor 14 in tiny increments along moving direction 22, as successive images are captured. Rapid calculation of image sharpness and other image characteristics enables image processor 20 to quickly determine the best focus. Automation of the image capture and focus adjustment process in this way enables an intra-oral image to be obtained quickly and minimizes the need for operator training and for subjective judgment.

The invention has been described in detail with particular reference to a presently preferred embodiment, but it will be understood that variations and modifications can be effected within the spirit and scope of the invention. For example, operator controls to initiate the image capture process have not been specifically shown, but can be provided on the body of auto-focus camera 10 or on a separate operator console. As is known to those skilled in the mechanical arts, mechanical coupling of linear piezoelectric actuator 16 to moveable sensor 14 for causing linear movement can be effected in a number of ways and may include a spring, linkage, or other component. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

1 target
10 auto-focus camera
12 optical system
14 moveable sensor
15 wire
16 piezoelectric actuator
18 driving system
20 image processor
22 moving direction
24. illumination system

What is claimed is:

1. An auto-focus camera comprising:
   an optical system for forming an image of a target;
   a moveable sensor for recording a set of one or more images of the target, the set of one or more images corresponding to a set of one or more positions for the moveable sensor;
   a linear piezoelectric actuator that is mechanically coupled to the moveable sensor for driving the moveable sensor to the set of one or more positions along a predetermined moving direction in response to a stimulus;
   a driving system actuable to generate the stimulus to drive the piezoelectric actuator; and
   an image processor that, in response to stored instructions, obtains the set of one or more recorded images from the moveable sensor, processes the set of one or more obtained recorded images, and identifies the image that is in focus, wherein the linear piezoelectric actuator moves at an average speed of 50-100 mm/s along the predetermined moving direction.

2. The auto-focus camera of claim 1, wherein the target is an intra-oral target.

3. The auto-focus camera of claim 1, wherein the width of the camera along a direction that is perpendicular to the predetermined moving direction is not greater than 5 mm.

4. The auto-focus camera of claim 1, wherein the piezoelectric actuator causes linear movement at an average step of 0.5-1.0 μm.

5. The auto-focus camera of claim 1, wherein the driving system comprises an integrated circuit driver.

6. The auto-focus camera of claim 1 further comprising an illuminating system for directing light to the target.

7. The auto-focus camera of claim 1, wherein the image that is in focus has the highest sharpness.

8. The auto-focus camera of claim 1, wherein the linear piezoelectric actuator is connected to the moveable sensor through a wire.

9. The auto-focus camera of claim 1, wherein forming the image is finished in not more than 0.2 second.

10. The auto-focus camera of claim 1, wherein the image processor further sends one or more pulses to the driving system, the number of the pulses corresponding to different positions for the moveable sensor.

11. An auto-focus camera comprising:
    an optical system for forming an image of a target;
    a moveable sensor for recording the image of the target,
    a linear piezoelectric actuator mechanically coupled to the moveable sensor for driving the moveable sensor along a predetermined moving direction in response to a stimulus;
    a driving system actuable to provide the stimulus to drive the piezoelectric actuator to move the moveable sensor; and
    an image processor that is connected to the driving system and the moveable sensor,
    wherein the linear piezoelectric actuator moves at an average speed of between 50-100 mm/s along the predetermined moving direction and the processor responds to stored instructions to actuate the driving system to generate the stimulus that drives the piezoelectric actuator, which in turn moves the moveable sensor to a preferred position where the sensor records and stores the image of the target.

12. The auto-focus camera of claim 11, wherein the target is an intra-oral target.

13. The auto-focus camera of claim 11, wherein the width of the camera along a direction that is perpendicular to the predetermined moving direction is not greater than 5 mm.

14. The auto-focus camera of claim 11, wherein the piezoelectric actuator causes linear movement at an average step of 0.5-1.0 µm.

15. The auto-focus camera of claim 11, wherein the driving system comprises an integrated circuit driver.

16. The auto-focus camera of claim 11 further comprising an illuminating system for directing light to the target.

17. The auto-focus camera of claim 11, wherein the image is a first image and wherein the sensor further records a second image and wherein the processor compares the first and second images for sharpness.

18. The auto-focus camera of claim 11, wherein the linear piezoelectric actuator is connected to the moveable sensor through a wire.

19. The auto-focus camera of claim 11, wherein forming the image is completed in not more than 0.2 second.

20. The auto-focus camera of claim 11, wherein the image processor sends one or more pulses to the driving system, the number of the pulses corresponding to the position of the moveable sensor relative to the preferred position.

* * * * *